United States Patent [19]

Baermann

[11] Patent Number: 4,549,532
[45] Date of Patent: Oct. 29, 1985

[54] FLEXIBLE MAGNETIC SHEET FOR THERAPEUTIC USE

[76] Inventor: Horst Baermann, Auf dem Saan 36, S-5064 Rosrath, Fed. Rep. of Germany

[21] Appl. No.: 629,364

[22] Filed: Jul. 10, 1984

[30] Foreign Application Priority Data

Jul. 14, 1983 [DE] Fed. Rep. of Germany ....... 3325356
Aug. 29, 1983 [DE] Fed. Rep. of Germany ....... 3331061

[51] Int. Cl.⁴ ............................................. A61N 1/42
[52] U.S. Cl. .................................... 128/1.3; 428/40; 428/900
[58] Field of Search .......................... 428/692, 40, 900; 128/1.3

[56] References Cited

U.S. PATENT DOCUMENTS

| | | | |
|---|---|---|---|
| 3,921,620 | 11/1975 | Nakayama | 128/1.3 |
| 4,162,672 | 7/1979 | Yazaki | 128/1.3 |
| 4,186,729 | 2/1980 | Harrison | 128/1.3 X |
| 4,374,516 | 2/1983 | Harrison | 128/1.3 |
| 4,391,270 | 7/1983 | Uragami | 128/1.3 |
| 4,480,596 | 11/1984 | Shumiyashu | 128/1.3 |
| 4,489,711 | 12/1984 | Latzke | 128/1.3 |

FOREIGN PATENT DOCUMENTS

| | | | |
|---|---|---|---|
| 4439 | of 1926 | Australia | 128/1.3 |
| 2335475 | 1/1975 | Fed. Rep. of Germany | 128/1.3 |
| 2506227 | 8/1976 | Fed. Rep. of Germany | 128/1.3 |
| 3147852 | 4/1983 | Fed. Rep. of Germany | |
| 0007405 | 1/1981 | Japan | 128/1.3 |
| 1665 | of 1872 | United Kingdom | 128/1.3 |
| 5111 | of 1883 | United Kingdom | 128/1.3 |

*Primary Examiner*—George F. Lesmes
*Assistant Examiner*—Nancy A. B. Swisher
*Attorney, Agent, or Firm*—Body, Vickers & Daniels

[57] ABSTRACT

A flexible magnetic sheet for therapeutic use made of a rubbery-flexible synthetic material in which permanent-magnetic ferrite particles have been embedded, the surface facing the body site to be treated of said sheet having been magnetized with magnetic poles of alternating polarities, which poles are in the form of some geometrical shape such as concentrically arranged rings, sectors, quadrangles and the like. Such sheet may also be composed of a plurality of individual parts.

16 Claims, 4 Drawing Figures

FLEXIBLE MAGNETIC SHEET FOR THERAPEUTIC USE

The present invention relates to permanent magnetic materials, and in particular, to flexible permanent magnetic sheets for therapeutic use.

Flexible permanent magnetic sheets have been used in the past for promoting blood circulation and body heating on peripheral body sites. As disclosed in German patent application No. 31 47 852, a flexible sheet of synthetic material in which permanent-magnetic particles of ferrite material have been embedded has an active surface which faces the body during use. The permanent magnetic particles are magnetized in parallel stripe-shaped magnetic poles of alternating polarity. For example, a magnetic north stripe is followed by a magnetic south stripe in alternating fashion. Further, such a sheet may be provided with a skin-compatible, self-adhering layer on the active magnetized surface for securing the sheet to the desired body site.

With regard to such sheets, it has been found that small electrical voltages and currents are induced in the body sites to be treated by magnetic fields of alternating polarity acting thereon. The magnetic fields cause the body sites to be heated and blood circulation to be promoted. This is particularly beneficial in the peripheral regions inasmuch as the blood flowing through the vessels at the site behaves like an electrically inductive medium. The therapeutical effect of such application is characterized by alleviation and removal of pain. However, this effect will only be achieved optimumly when poles of alternating polarity extend in a direction transverse to the blood flow direction. Thus, the stripe shaped poles hereinabove described are unidirectional in pole orientation. Thus, only a single orientation of the stripes will produce the desired therapeutic effect. Inasmuch as such sheets do not enable the user to determine the direction in which the stripe shaped poles are arrayed, the sheet may be improperly oriented in use with resultant minimization or elimination of the therapeutic effect. In other words, the user does not know whether or not the sheet is properly applied to the body site in a way to ensure the desired optimum therapeutic effect. This is particularly disadvantageous inasmuch as such magnetic sheets can be readily acquired for therapeutical use without prescription by untrained personnel not knowing of the above interdependencies. However, the stripe shaped sheets do not exhibit therapeutic effects on blood vessels not extending substantially transversely thereto. Accordingly, at body sites having vessels of varying orientations, the therapeutic effect is limited.

BRIEF SUMMARY OF THE INVENTION

The above and other disadvantages of prior sheet constructions are overcome by the present invention which provides a permanent magnetic sheet which can be universally oriented on the body site while retaining the therapeutic effects provided thereby. More particularly, the present invention provides a flexible, permanent magnetic sheet which may be attached to the body site to be treated in any operational position without particular instruction or special knowledge for providing optimum therapeutic effects. These advantages are attained by using an array of magnetic poles of alternating polarity formed into a geometrical shape wherein the poles on the sheet are arranged in areas oriented concentrically, angularly or radially with respect to the poles of the opposite polarity.

In one advantageous embodiment of the present invention, the magnetic sheet is provided with magnetic poles arrayed in the shape of concentric rings of alternating polarity. In another embodiment, the magnetic poles are present in an array in a shape of sectors, the polarities of which alternate circumferentially. In a further embodiment, the magnetic sheet comprises a plurality of individual, flexible sheet elements having poles alternating polarity and the elements are connected to each other by means of a flexible nonmagnetic, self-adhesive sheet. The sheet elements may be in the form of sectors with poles alternating in a radially outwardly extending direction.

With each of the above described embodiments, it is ensured that magnetic poles of alternating polarity will act on the various blood vessels on the body site regardless of the orientation of the sheet thereon. Thus, the therapeutic effect, as compared to the prior constructions, is not limited to only one direction of blood flow, and as applied provides therapeutic effect for all blood flow directions. This is particularly advantageous to the vascular systems in the peripheral skin regions. The magnetic sheets of the present invention may also be beneficially provided with magnetic poles of differing widths. Further, a sheet may be provided with a metallic coating on at least one surface thereof in order to retain or reflect body heat. Such a metallic coating can be applied, for example, by vapor deposition. A protective layer such as a varnish, may be applied over the metallic coating to limit the wear thereof.

These and other advantages of the present invention will become apparent from the following description taken in conjunction with the drawings accompanying this disclosure.

BRIEF DESCRIPTION OF THE DRAWINGS

In this disclosure, the following drawings are incorporated.

DETAILED DESCRIPTION OF THE INVENTION

Figure 1:
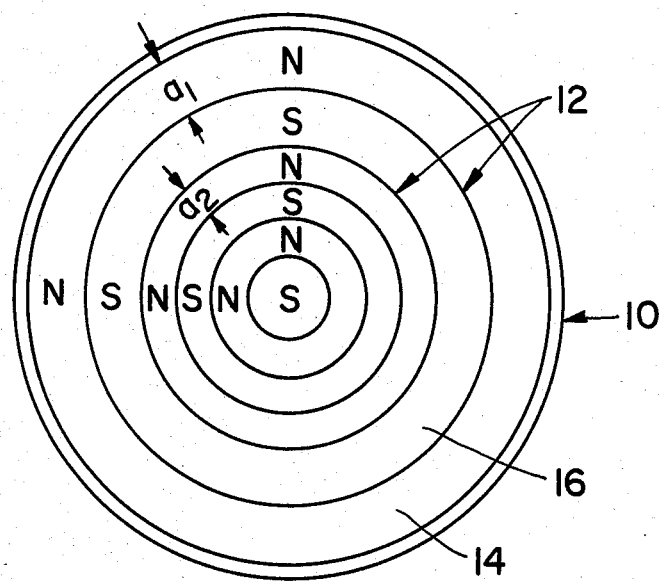
FIG. 1 is a top plan view of a flexible magnetic sheet according to one embodiment of the present invention showing a concentric ring array of alternating magnetic poles.

Referring to the drawings for purposes of illustrating the preferred embodiments only and not limiting same, FIG. 1 shows a flexible magnetic sheet 10 for therapeutic use. The sheet 10 is circular in plan view and is formed of a suitable rubbery-flexible synthetic material which is compatible with the skin and in which permanent-magnetic particles are embedded. In a known manner, the particles for example, may comprise barium ferrite or strontium ferrite. The thickness of the sheet 10 is such that the same remains flexible in use while generally comfortable to the surface to be treated. At the same time, the thickness should be such that sufficient particles may be embedded in the active surface for the intended application. The diameter of the sheet may vary according to the intended application ranging from sizes sufficient for local application to sizes compatible with significant body coverage.

The magnetic particles in the active surface of the sheet 10 adapted to face the user in the sheet, are selectively magnetized in a known manner to establish a plurality of concentric rings 12 providing alternating angular north poles 14 and south poles 16. Thus, there is a central circular area of south polarity and radially outwardly extending rings of sequentially alternating north and south polarities. The rings may be constant with or may have differing pole widths $a_1$, $a_2$.

Figure 2:
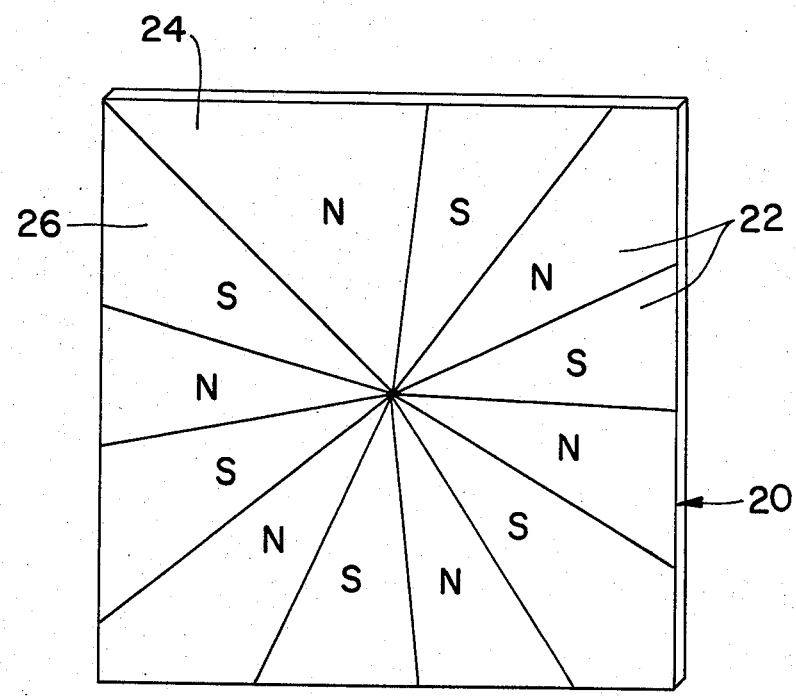
FIG. 2 is a top plan view of another embodiment showing a sector shape array of alternating magnetic poles.

Referring to FIG. 2, a flexible magnetic sheet 20 of the type hereinabove described, has permanent magnetic particles embedded in the active surface thereof, which have been magnetized to establish an array of radially diverging sectors 22 having triangular north poles 24 and south poles 26 which alternate circumferentially. The peripheral shape of the sheet 20 in plan view is square, however, it will be appreciated that the sheet and the shape of other embodiments may be circular or any other planar configuration desired.

Figure 3:
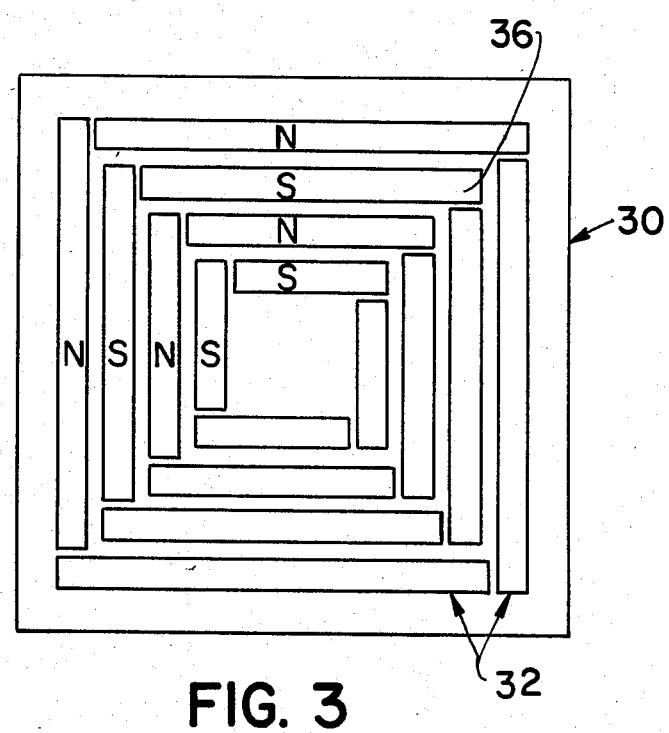
FIG. 3 is a top plan view of a further embodiment showing an array of magnetic poles comprising concentric quadrangles; and, FIG. 4 is a top plan view of yet another embodiment showing a composite structure of magnetic sheet elements.

Referring to FIG. 3, a flexible magnetic sheet 30 of the type hereinabove described, has permanent magnetic particles embedded in the active surface thereof which have been magnetized to provide an array of generally rectangular magnetic poles arranged in concentric quadrangular sets. The sheet 30 in plan view is square and each pole set is comprised of 4 mutually perpendicular, rectangular poles 32 which are equally spaced from the center of the sheet. The north poles 34 are parallel to the south poles 36 of the adjoining sets. The individual poles may abut at the corners or as illustrated, may be slightly spaced from one another.

Figure 4:
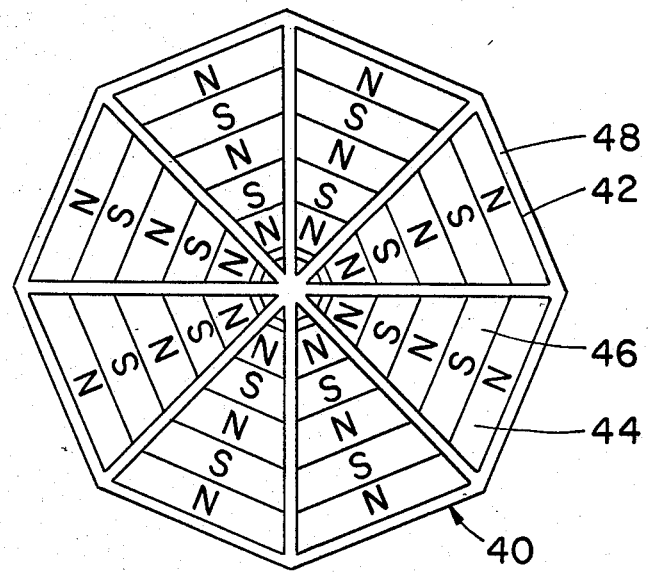

Referring to FIG. 4, a flexible magnetic sheet 40 is generally octagonal in plan view and is comprised of eight triangular sheet elements 42. Each sheet element 42 includes radially outwardly alternating north poles 44 and south poles 46. The sheet elements 42 are overlayed and interconnected by a self-adhesive layer 48. In completed array, the poles of common polarity are angularly related in a concentric arrangement.

The poles of the above described arrays may be in the form of other geometrical shapes as long as they are related concentrically, angularly or radially with respect to each other so that their alternating polarities will be traversed by blood flow vessels when universally oriented on the body. For the purpose of attaching these sheets to the skin, a known skin-compatible, self-adhesive coating, not shown in the drawings, may be provided on the active surface adjacent the user. Until time of use, the self-adhesive coating may be protected by removable silicon paper cover. Further, the magnetic sheets hereinabove described may be secured by means of separately added, skin-compatible plasters. Also, in order to retain or reflect body heat, the sheets may be provided with a metallic coating on the side opposite the user which may be applied by laminating or by vapor deposition. Such a metal coating may be additionally covered by a protective layer, such as varnish, to avoid water thereof.

I claim:

1. A flexible magnetic sheet for therapeutic use by application to a body site comprising:
   a flexible sheet composed of a skin compatible synthetic material having an active surface with permanent magnetic particles of a ferrite material embedded therein; a first plurality of areas on said active surface having the permanent magnetic particles magnetized to form north poles with respect to said active surface; a second plurality of areas on said active surface closely adjacent said first plurality of areas having the permanent particles magnetized to form south poles with respect to said active surface, the north poles and south poles being arranged in a concentric, angular or radial geometrical pattern thereby establishing magnetic fields having angularities with respect to a line traversing the active surface such that alternating polarities will be traversed by blood flow vessels notwithstanding universal orientation of the body means on the body site.

2. The flexible magnetic sheet as recited in claim 1 wherein said geometrical pattern is formed by concentric rings of alternating polarity.

3. The flexible magnetic sheet as recited in claim 2, wherein the rings have varying widths.

4. The flexible magnetic sheet as recited in claim 1, wherein the areas are in the form of sectors of alternating polarity.

5. The flexible magnetic sheet as recited in claim 4, wherein the sectors having varying widths.

6. The flexible magnetic sheet as recited in claim 1, wherein said body means include a plurality of interconnected elements, each having areas of alternating polarity.

7. The flexible magnetic sheet as recited in claim 6, wherein said elements are interconnected by a flexible nonmagnetic sheet.

8. The flexible magnetic sheet as recited in claim 1, wherein a metallic coating is applied on the surface of said body means opposite said active surface.

9. The flexible magnetic sheet as recited in claim 8, wherein said metallic coating is applied by vapor-deposition.

10. The flexible magnetic sheet as recited in claim 9, wherein a protective layer is applied over said metallic coating.

11. The flexible magnetic sheet as recited in claim 1 wherein said geometrical pattern is formed by concentric polygons.

12. The flexible magnetic sheet as recited in claim 11, said polygons are squares.

13. The flexible magnetic sheet as recited in claim 1 wherein said polygons are octagons.

14. The flexible magnetic sheet as recited in claim 1 wherein said geometrical pattern consists of a plurality of concentric strips which are continuous and of a constant width.

15. The flexible magnetic sheet as recited in claim 1 wherein said concentric strips are a plurality of constant width rings.

16. The flexible magnetic sheet recited in claim 1 wherein said ferrite material is selected from the group consisting of barium ferrite, strontium ferrite or mixtures thereof.

* * * * *

REEXAMINATION CERTIFICATE (3596th)

United States Patent [19]

Baermann

[11] B1 4,549,532

[45] Certificate Issued Aug. 11, 1998

[54] FLEXIBLE MAGNETIC SHEET FOR THERAPEUTIC USE

[75] Inventor: Horst Baermann, Rosrath, Germany

[73] Assignee: Baermann Magnetics, Inc.

Reexamination Requests:
No. 90/003,344, Feb. 25, 1994
No. 90/003,369, Mar. 25, 1994
No. 90/003,697, Jan. 20, 1995

Reexamination Certificate for:
Patent No.: 4,549,532
Issued: Oct. 29, 1985
Appl. No.: 629,364
Filed: Jul. 10, 1984

[30] Foreign Application Priority Data

| Jul. 14, 1983 | [DE] | Germany | 3325356 |
| Aug. 29, 1983 | [DE] | Germany | 3331061 |

[51] Int. Cl.$^6$ .................................................. A61N 2/08
[52] U.S. Cl. ................... 600/15; 428/40.9; 428/900
[58] Field of Search .................................... 600/15

[56] References Cited

U.S. PATENT DOCUMENTS

| Re. 29,451 | 10/1977 | Baermann . | | |
| 2,576,679 | 11/1951 | Guillaud | .................. | 175/21 |
| 2,762,777 | 9/1956 | Went et al. | .................. | 252/62.5 |
| 2,959,832 | 11/1960 | Baermann . | | |
| 3,051,988 | 9/1962 | Baermann . | | |
| 3,136,720 | 6/1964 | Baermann . | | |
| 3,187,151 | 6/1965 | Baermann . | | |
| 3,191,106 | 6/1965 | Baermann . | | |
| 3,229,030 | 1/1966 | Baermann . | | |
| 3,921,620 | 11/1975 | Nakayama . | | |
| 4,162,672 | 7/1979 | Yazaki . | | |
| 4,186,729 | 2/1980 | Harrison | .................. | 128/1.3 |
| 4,374,516 | 2/1983 | Harrison | .................. | 128/1.3 |
| 4,391,270 | 7/1983 | Uragami | .................. | 128/1.3 |
| 4,480,596 | 11/1984 | Shumiyashi . | | |
| 4,489,711 | 12/1984 | Latzke | .................. | 600/15 |

FOREIGN PATENT DOCUMENTS

| 4439 | of 1926 | Australia . |
| 10610 | 9/1970 | Australia . |
| 0081109 | 6/1983 | European Pat. Off. . |
| 0134437 | 3/1985 | European Pat. Off. . |
| 1215110 | 4/1960 | France . |
| 2371916 | 6/1978 | France . |
| 56-19817405 | 1/1981 | Japan . |
| 56-7405 | 1/1981 | Japan . |
| 1665 | of 1872 | United Kingdom . |
| 5111 | of 1883 | United Kingdom . |

OTHER PUBLICATIONS

Gessner G. Hawley, *The Condensed Chemical Dictionary*, p. 1076 (10th Ed. 1981).

R. S. Tebble & D. J. Craik, *Magnetic Materials*, pp. 412–413, 450–451 (published 1969).

Ted Zablotsky, M.D., Letter, dated Jun. 10th, 1992, to AMERIflex, Inc. (Best Available Copy).

*Primary Examiner*—Lee S. Cohen

[57] ABSTRACT

A flexible magnetic sheet for therapeutic use made of a rubbery-flexible synthetic material in which permanent-magnetic ferrite particles have been embedded, the surface facing the body site to be treated of said sheet having been magnetized with magnetic poles of alternating polarities, which poles are in the form of some geometrical shape such as concentrically arranged rings, sectors, quadrangles and the like. Such sheet may also be composed of a plurality of individual parts.

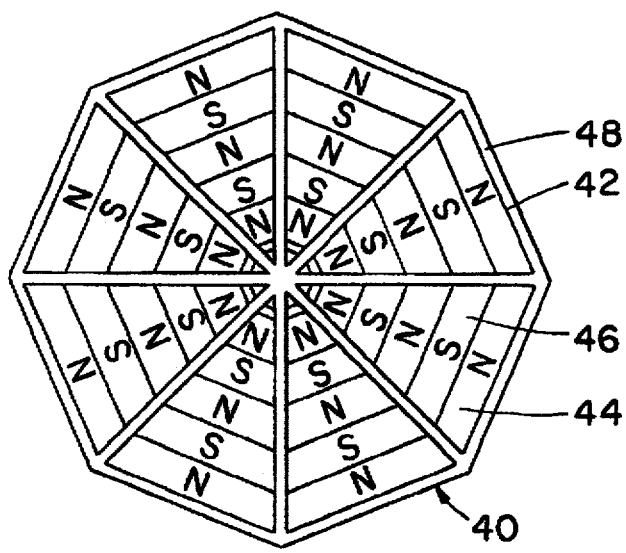

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 4, 6–12 and 16 are cancelled.

Claims 3, 5, 13, 14 and 15 are determined to be patentable as amended.

3. [The flexible magnetic sheet as recited in claim 2, wherein the rings have] *A flexible magnetic sheet for therapeutic use by application to a body site comprising:*

*a flexible sheet composed of a skin compatible synthetic material having an active surface with permanent magnetic particles of a ferrite material embedded therein; a first plurality of areas on said active surface having the permanent magnetic particles magnetized to form north poles with respect to said active surface; a second plurality of areas on said active surface closely adjacent said first plurality of areas having the permanent particles magnetized to form south poles with respect to said active surface, the north poles and south poles being arranged in a concentric, angular, or radial geometrical pattern thereby establishing magnetic fields having angularities with respect to a line traversing the active surface such that alternating polarities will be traversed by blood flow vessels notwithstanding universal orientation of said flexible sheet on the body site, said geometrical pattern being provided by concentric rings of alternating polarity and varying widths.*

5. [The flexible magnetic sheets as recited in claim 4, wherein the sectors having] *A flexible magnetic sheet for therapeutic use by application to a body site comprising:*

*a flexible sheet composed of a skin compatible synthetic material having an active surface with permanent magnetic particles of a ferrite material embedded therein; a first plurality of areas on said active surface having the permanent magnetic particles magnetized to form north poles with respect to said active surface; a second plurality of areas on said active surface closely adjacent said first plurality of areas having the permanent particles magnetized to form south poles with respect to said active surface, the north poles and south poles being arranged in a concentric, angular, or radial geometrical pattern thereby establishing magnetic fields having angularities with respect to a line traversing the active surface such that alternating polarities will be traversed by blood flow vessels notwithstanding universal orientation of said flexible sheet on the body site, the areas being in the form of sectors of alternating polarity and varying widths.*

13. [The flexible magnetic sheet as recited in claim 11, wherein said polygons are] *A flexible magnetic sheet for therapeutic use by application to a body site comprising:*

*a flexible sheet composed of a skin compatible synthetic material having an active surface with permanent magnetic particles of a ferrite material embedded therein; a first plurality of areas on said active surface having the permanent magnetic particles magnetized to form north poles with respect to said active surface; a second plurality of areas on said active surface closely adjacent said first plurality of areas having the permanent particles magnetized to form south poles with respect to said active surface, the north poles and south poles being arranged in a concentric, angular, or radial geometrical pattern thereby establishing magnetic fields having angularities with respect to a line traversing the active surface such that alternating polarities will be traversed by blood flow vessels notwithstanding universal orientation of said flexible sheet on the body site, said geometrical pattern being provided by concentric octagons.*

14. [The flexible magnetic sheet as recited in claim 1, wherein] *A flexible magnetic sheet for therapeutic use by application to a body site comprising:*

*a flexible sheet composed of a skin compatible synthetic material having an active surface with permanent magnetic particles of a ferrite material embedded therein; a first plurality of areas on said active surface having the permanent magnetic particles magnetized to form north poles with respect to said active surface; a second plurality of areas on said active surface closely adjacent said first plurality of areas having the permanent particles magnetized to form south poles with respect to said active surface, the north poles and south poles being arranged in a concentric, angular, or radial geometrical pattern thereby establishing magnetic fields having angularities with respect to a line traversing the active surface such that alternating polarities will be traversed by blood flow vessels notwithstanding universal orientation of said flexible sheet on the body site,* said geometrical pattern [consists] *consisting* of a plurality of concentric strips which are continuous and of a constant width.

15. The flexible magnetic sheet as recited in claim [1] *14* wherein said concentric strips are a plurality of constant width rings.

* * * * *